(12) United States Patent
Knoesche et al.

(10) Patent No.: US 8,809,575 B2
(45) Date of Patent: Aug. 19, 2014

(54) PROCESS FOR PREPARING ISOCYANATES

(75) Inventors: Carsten Knoesche, Niederkirchen (DE); Torsten Mattke, Freinsheim (DE); Patric Mueller, Mutterstadt (DE)

(73) Assignee: BASF SE, Ludwigshafen (DE)

( * ) Notice: Subject to any disclaimer, the term of this patent is extended or adjusted under 35 U.S.C. 154(b) by 456 days.

(21) Appl. No.: 13/131,123

(22) PCT Filed: Nov. 30, 2009

(86) PCT No.: PCT/EP2009/066023
§ 371 (c)(1),
(2), (4) Date: May 25, 2011

(87) PCT Pub. No.: WO2010/063665
PCT Pub. Date: Jun. 10, 2010

(65) Prior Publication Data
US 2011/0257428 A1  Oct. 20, 2011

(30) Foreign Application Priority Data
Dec. 3, 2008 (EP) .................... 08170576

(51) Int. Cl.
C07C 263/10 (2006.01)
(52) U.S. Cl.
CPC .................... *C07C 263/10* (2013.01)
USPC ........................................ 560/347
(58) Field of Classification Search
CPC ...................................... C07C 263/10
USPC ........................................ 560/347
See application file for complete search history.

(56) References Cited

U.S. PATENT DOCUMENTS

| | | | | |
|---|---|---|---|---|
| 3,274,225 A | * | 9/1966 | Saunders et al. | 560/347 |
| 4,549,991 A | * | 10/1985 | Disteldorf et al. | 560/347 |
| 2004/0068137 A1 | | 4/2004 | Herold et al. | |
| 2008/0027242 A1 | | 1/2008 | Knosche et al. | |
| 2008/0167490 A1 | | 7/2008 | Pohl et al. | |

FOREIGN PATENT DOCUMENTS

| | | |
|---|---|---|
| DE | 10 2006 058 634 | 6/2008 |
| EP | 1 319 655 | 6/2003 |
| EP | 1 403 248 | 3/2004 |
| EP | 1 555 258 | 7/2005 |
| EP | 1 935 875 | 6/2008 |
| WO | 2005 123665 | 12/2005 |
| WO | 2007 028715 | 3/2007 |

OTHER PUBLICATIONS

International Search Report Issued Mar. 2, 2010 in PCT/EP09/066023 filed Nov. 30, 2009.

* cited by examiner

*Primary Examiner* — Rosalynd Keys
(74) *Attorney, Agent, or Firm* — Oblon, Spivak, McClelland, Maier & Neustadt, L.L.P.

(57) ABSTRACT

The invention relates to a process for preparing isocyanates by reacting the corresponding amines with phosgene in the gas phase, optionally in the presence of an inert medium, in which the amine and the phosgene are first mixed and converted to the isocyanate in a reactor, and in which a reaction gas (1) which comprises isocyanate and hydrogen chloride leaving the reactor is cooled in a quench (3) by adding a liquid quench medium (5) to form a mixture of reaction gas and quench medium as the product stream (7). The quench medium (5) used is a mixture which comprises at least one solvent and isocyanate and which is withdrawn from the preparation process, any solid particles present in the quench medium (5) being removed before addition to the quench (3).

19 Claims, 1 Drawing Sheet

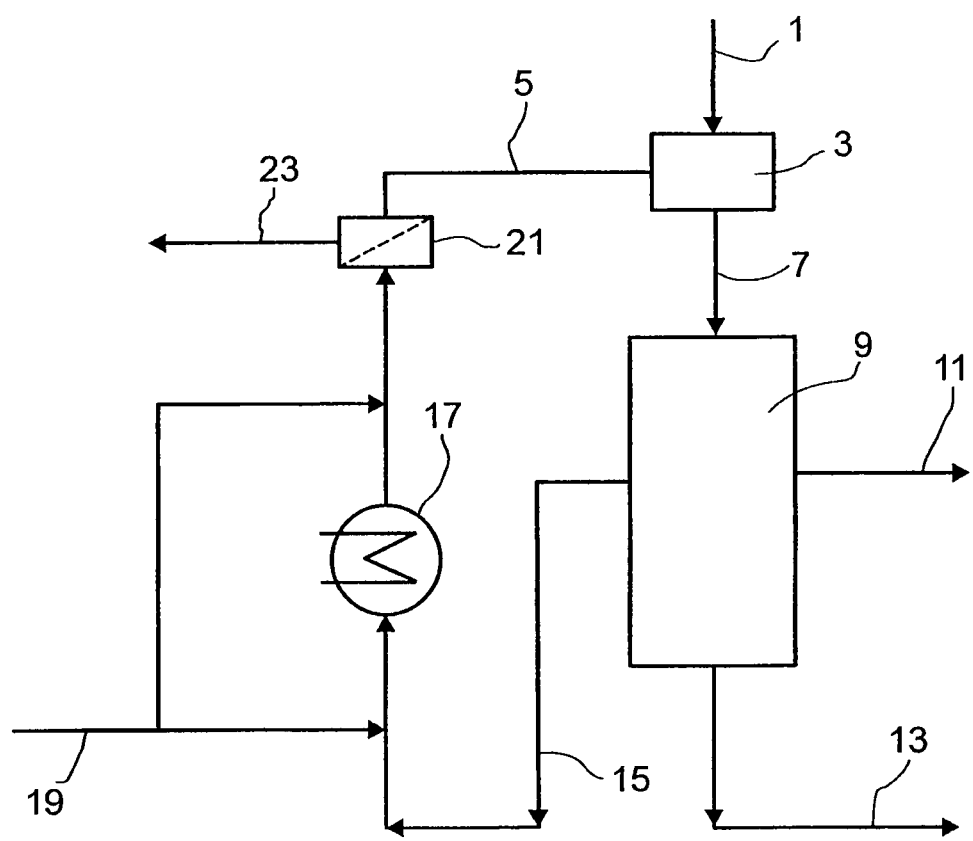

PROCESS FOR PREPARING ISOCYANATES

The invention relates to a process for preparing isocyanates by reacting the corresponding amines with phosgene in the gas phase, optionally in the presence of an inert medium, in which the amine and the phosgene are first mixed and converted to the isocyanate in a reactor. A reaction gas which comprises isocyanate and hydrogen chloride leaving the reactor is cooled in a quench by adding a liquid quench medium to form a mixture of reaction gas and quench medium as the product stream.

The preparation of isocyanates by phosgenating the corresponding amines can in principle be effected by a liquid phase or gas phase phosgenation. Gas phase phosgenation is notable in that a higher selectivity, a lower holdup of toxic phosgene and a reduced amount of energy are required.

In gas phase phosgenation, an amine-containing reactant stream and a phosgene-containing reactant stream, each in the gaseous state, are mixed. The amine and the phosgene react with release of hydrogen chloride (HCl) to give the corresponding isocyanates. The amine-containing reactant stream is generally present in the liquid phase and has to be evaporated and optionally superheated before being mixed with the phosgene-containing stream.

Corresponding processes for preparing isocyanates in the gas phase are described, for example, in EP-A 1 319 655 or EP-A 1 555 258.

In order to prevent further reactions, it is necessary to cool the reaction mixture rapidly after the end of the reaction. To this end, for example, a liquid quench is used. Such a liquid quench is described, for example, in EP-A 1 403 248 or in DE-A 10 2006 058 634. The quench medium which is added for cooling has a temperature which is in the range from 50 to 200° C. The liquid stream sprayed in cools the reaction gas rapidly to temperatures generally between 100 and 200° C. This forms a biphasic mixture with an isocyanate-rich liquid phase and a low-isocyanate gas phase. The two are then sent to a common separating stage or optionally separate separating stages, for example a distillation stage for separation of hydrogen chloride and phosgene on the one hand, and isocyanate, possibly with solvent, on the other hand.

A process in which the isocyanate prepared is also present in the quench medium is described in EP-A 1 935 875. As a result of the isocyanate content in the quench medium, it is possible to achieve a higher isocyanate concentration in the product stream which leaves the quench and is to be purified later. A disadvantage of this process in which isocyanate is present in the quench medium is, however, that solids can arise through degradation of the starting materials and/or of the reaction products and are entrained into the downstream plant parts. The solids accumulate in the high boiler streams and are generally discharged via column bottoms. Since, however, liquid is withdrawn as quench medium from the high boiler streams, solid particles may be present in the quench medium. These can lead to deposits in the downstream plant parts. The solid constituents and the deposits can block pipelines, regulating devices and other apparatus parts. More particularly, the atomizing nozzles of the quench can become blocked. This requires costly and inconvenient cleaning of the plant.

It is an object of the present invention to provide a process for preparing isocyanates by reacting the corresponding amines with phosgene, in which the quench medium is recycled at least partly into the process after workup and may optionally comprise isocyanate, which achieves a higher service life than in the processes known from the prior art.

The object is achieved by a process for preparing isocyanates by reacting the corresponding amines with phosgene in the gas phase, optionally in the presence of an inert medium, in which the amine and the phosgene are first mixed and converted to the isocyanate in a reactor, and in which a reaction gas which comprises isocyanate and hydrogen chloride leaving the reactor is cooled in a quench by adding a liquid quench medium to form a mixture of reaction gas and quench medium as the product stream. The quench medium used is a mixture which comprises at least one solvent or isocyanate and which is withdrawn from a workup process connected downstream of the reaction, any solid particles present in the quench medium being removed before addition to the quench.

The removal of the solid particles which may be present in the quench medium before addition of the quench medium to the quench prevents solid particles present in the quench medium from being deposited in the nozzles, thus leading to blockage of the nozzles. This can increase the service life of the quench compared to the processes known from the prior art.

To prepare the isocyanate, the phosgene and the amine are preferably first fed to a mixing zone in which amine and phosgene are mixed to give a reaction mixture. Subsequently, the reaction mixture is fed to the reactor in which the conversion to the isocyanate is effected. The conversion of amine and phosgene in the reactor preferably proceeds in the gas phase. To this end, the pressure in the reactor is preferably in the range between 0.3 and 3 bar absolute, more preferably in the range from 0.8 to 3.0 bar absolute. The temperature is preferably in the range from 250 to 550° C., especially in the range from 300 to 500° C.

In order to be able to perform the reaction in the gas phase, it is also preferred to add the amine and the phosgene in gaseous form. To this end, the amine preferably has a temperature in the range from 200 to 400° C. The pressure of the amine added is preferably in the range between 0.05 and 3 bar absolute. The temperature of the phosgene added is preferably in the range from 250 to 450° C. To this end, the phosgene is typically heated before addition in the manner known to those skilled in the art.

To heat the phosgene and the amine and to evaporate the amine, for example, electrical heating or direct or indirect heating by combustion of a fuel is used. The fuels used are typically fuel gases, for example natural gas. By virtue of the lowering of the boiling temperature of the amine by lowering the pressure, however, heating is also possible, for example by means of steam. The pressure of the steam is selected here according to the boiling temperature of the amine. A suitable vapor pressure of the steam is, for example, in the range from 40 to 100 bar. This gives rise to a temperature of the steam in the range from 250 to 311° C.

In general, it is necessary to heat the amine to the reaction temperature in a plurality of stages. In general, the amine, for this purpose, is first preheated, then evaporated and then superheated. In general, the evaporation takes the longest residence times and thus leads to decomposition of the amine. In order to minimize this, evaporation at lower temperatures, as arises, for example, through the lower pressure, is advantageous. In order to superheat the evaporated amine to reaction temperature after the evaporation, heating with steam is generally insufficient. For superheating, electrical heating or direct or indirect heating by combustion of a fuel is therefore typically used.

In contrast to the evaporation of the amine, the phosgene is evaporated generally at significantly lower temperatures. For this reason, the phosgene can generally be evaporated using steam. Alternatively, the evaporation of the phosgene can also be effected by means of thermal integration, by, for example, utilizing the heat obtained in the quench to evaporate the phosgene. This allows the evaporation to be accomplished with overall energy neutrality. In addition to the heat obtained in the quench, it is also possible to utilize any other stream which has a higher temperature than the evaporation temperature of the phosgene. These are, for example, condensate streams obtained in a condensation which follows the quench. However, the necessary superheating of the phosgene to heat it to reaction temperature is generally also possible only by electrical heating or direct or indirect heating by combustion of a fuel.

The reactor which is used for phosgenation of the amine to prepare isocyanates is known to those skilled in the art. In general, the reactors used are tubular reactors. In the reactor, the amine is reacted with the phosgene to give the corresponding isocyanate and hydrogen chloride. Typically, the phosgene is added in excess, such that the reaction gas which forms in the reactor, as well as the isocyanate formed and the hydrogen chloride, also comprises phosgene.

Amines which can be used to prepare isocyanates are monoamines, diamines, triamines or higher-functionality amines. Preference is given to using monoamines or diamines. According to the amine used, the corresponding monoisocyanates, diisocyanates, triisocyanates or higher-functionality isocyanates are obtained. Preference is given to preparing monoisocyanates or diisocyanates by the process according to the invention.

Diamines and diisocyanates may be aliphatic, cycloaliphatic or aromatic.

Cycloaliphatic isocyanates are those which comprise at least one cycloaliphatic ring system.

Aliphatic isocyanates are those which have exclusively isocyanate groups bonded to straight or branched chains.

Aromatic isocyanates are those which have at least one isocyanate group bonded to at least one aromatic ring system.

The term "(cyclo)aliphatic isocyanates" is used hereinafter for cycloaliphatic and/or aliphatic isocyanates.

Examples of aromatic mono- and diisocyanates are preferably those having 6 to 20 carbon atoms, for example phenyl isocyanate, monomeric 2,4'- and/or 4,4'-methylene-di(phenyl isocyanate) (MDI), 2,4- and/or 2,6-tolylene diisocyanate (TDI) and 1,5- or 1,8-naphthyl diisocyanate (NDI).

Examples of (cyclo)aliphatic diisocyanates are aliphatic diisocyanates such as 1,4-tetramethylene diisocyanate, 1,6-hexamethylene diisocyanate (1,6-diisocyanatohexane), 1,8-octamethylene diisocyanate, 1,10-decamethylene diisocyanate, 1,12-dodecamethylene diisocyanate, 1,14-tetradecamethylene diisocyanate, 1,5-diisocyanatopentane, neopentane diisocyanate, derivatives of lysine diisocyanate, tetramethylxylylene diisocyanate (TMXDI), trimethylhexane diisocyanate or tetramethylhexane diisocyanate, and 3(or 4),8(or 9)-bis(isocyanatomethyl)tricyclo-[5.2.1.0$^{2.6}$]decane decane isomer mixtures, and cycloaliphatic diisocyanates such as 1,4-, 1,3- or 1,2-diisocyanatocyclohexane, 4,4'- or 2,4'-di(isocyanatocyclohexyl)methane, 1-isocyanato-3,3,5-trimethyl-5-(isocyanatomethyl)cyclohexane (isophorone diisocyanate), 1,3- or 1,4-bis(isocyanatomethyl)cyclohexane, 2,4- or 2,6-diisocyanato-1-methylcyclohexane.

Preferred (cyclo)aliphatic diisocyanates are 1,6-diisocyanatohexane, 1-isocyanato-3,3,5-trimethyl-5-(isocyanatomethyl)cyclohexane and 4,4'-di(isocyanatocyclohexyl)-methane. Particular preference is given to 1,6-diisocyanatohexane, 1-isocyanato-3,3,5-trimethyl-5-(isocyanatomethyl)cyclohexane, 1,5-diisocyanatopentane and 4,4'-di(isocyanatocyclohexyl)methane.

Examples of aromatic diisocyanates are 2,4-, 2,6-tolylene diisocyanate, methylenediphenyl isocyanate or isomer mixtures thereof.

Amines which are used in the process according to the invention for reaction to give the corresponding isocyanates are those in which the amine, the corresponding intermediates and the corresponding isocyanates are present in gaseous form under the selected reaction conditions. Preference is given to amines which decompose over the duration of the reaction under the reaction conditions to an extent of at most 2 mol %, more preferably to an extent of at most 1 mol % and most preferably to an extent of at most 0.5 mol %. Particularly suitable amines here are especially diamines based on aliphatic or cycloaliphatic hydrocarbons having 2 to 18 carbon atoms. Examples thereof are 1,6-diaminohexane, 1,5-diaminopentane, 1,3-bis(amino-methyl)cyclohexane, 1-amino-3,3,5-trimethyl-5-aminomethylcyclohexane (IPDA) and 4,4-diaminodicyclohexylmethane. Preference is given to using 1,6-diaminohexane (HDA) and 1,5-diaminopentane.

For the process according to the invention, it is likewise possible to use aromatic amines which can be converted to the gas phase without significant decomposition. Examples of preferred aromatic amines are tolylenediamine (TDA), as the 2,4 or 2,6 isomer or as a mixture thereof, for example as an 80:20 to 65:35 (mol/mol) mixture, diaminobenzene, 2,6-xylidine, naphthyldiamine (NDA) and 2,4'- or 4,4'-methylene (diphenyldiamine) (MDA) or isomer mixtures thereof. Among these preference is given to the diamines, particular preference to 2,4- and/or 2,6-TDA or 2,4'- and/or 4,4'-MDA.

To prepare monoisocyanates, it is likewise possible to use aliphatic, cycloaliphatic or aromatic amines, typically monoamines. A preferred aromatic monoamine is especially aniline.

In the gas phase phosgenation, it is desirable that the compounds which occur in the course of the reaction, i.e. reactants (amine and phosgene), intermediates (especially the mono- and dicarbamoyl chlorides which form as intermediates), end products (isocyanate), and any inert compounds metered in, remain in the gas phase under the reaction conditions. Should these or other components be deposited from the gas phase, for example on the reactor wall or other apparatus components, these deposits can undesirably alter the heat transfer or the flow through the components affected. This is especially true of occurrence of the amine hydrochlorides which form from free amino groups and hydrogen chloride, since the resulting amine hydrochlorides precipitate readily and are re-evaporable only with difficulty.

In addition to the use of a tubular reactor, it is also possible to use essentially cuboidal reaction chambers, for example plate reactors. Any desired different cross section of the reactor is also possible.

In order to prevent the formation of by-products, it is preferred to supply phosgene in excess. In order to supply only the proportion of amines needed for the reaction, it is possible to mix the amine with an inert gas. The proportion of inert gas in the amine can be used to adjust the amount of the amine supplied for a given geometry of the feed orifices for the amine and the phosgene. Inert media which can be added are those which are present in gaseous form in the reaction chamber and do not react with the compounds which occur in the course of the reaction. The inert media used may, for example, be nitrogen, noble gases such as helium or argon, aromatics such as chlorobenzene, o-dichlorobenzene, trichlorobenzene, toluene, xylene, chloronaphthalene, decahydronaphthalene, carbon dioxide or carbon monoxide. Preference is given, however, to using nitrogen and/or chlorobenzene as the inert medium.

Alternatively, it is, however, also possible, for example, in order to avoid too great an excess of phosgene, to add the inert medium to the phosgene.

In general, the inert medium is added in an amount such that the ratio of the gas volumes of inert medium to amine or to phosgene is less than 0.0001 to 30, preferably less than 0.01 to 15 and more preferably less than 0.1 to 5.

In order to reduce or to prevent the formation of undesired by-products, and also to suppress decomposition of the isocyanate formed, the reaction gas is cooled in a quench immediately after the reaction. To this end, a preferably liquid quench medium is added. As a result of heating or evaporation of the quench medium, it absorbs heat and leads to rapid cooling of the reaction gas.

According to the invention, the quench medium comprises at least a portion of the mixture leaving the quench. This generally comprises any solvent used, isocyanate formed in the reaction, and possibly residues of phosgene and HCl.

In order to prevent deposits from forming in pipelines, regulating devices and other apparatus parts, especially in the atomizer nozzles of the quench, any solid particles present in the quench medium are removed before addition to the quench.

In a first embodiment, the solid particles which may be present in the quench medium are removed from the quench medium in a hydrocyclone or a filter. The filter or the hydrocyclone may be positioned at any desired point upstream of the atomizer nozzles.

When a filter is used to remove the solid particles which may be present in the quench medium, any desired filter known to those skilled in the art is suitable. Suitable filters are, for example, continuous and also batchwise apparatus such as surface or depth filters, for example, screen filters, suction filters, candle filters, leaf filters, depth filters, chamber filters and membrane filters. These filters can be operated by means of pressure (pressure filters) or by means of reduced pressure (suction filters).

In addition to filters, it is also possible to use centrifuges, for example peeler centrifuges, disk centrifuges, screen centrifuges or pusher centrifuges, or gravitational separators, to remove particular constituents.

In an alternative embodiment, the solid particles which may be present in the quench medium are removed from the quench medium by evaporation and recondensation. The evaporation converts liquid constituents of the quench medium to the vapor phase, which are subsequently condensed out again. Solid particles and high-boiling constituents are removed in this way. The evaporation and recondensation can be performed, for example, in a distillation column. Alternatively, it is also possible to use any desired evaporator for the evaporation and to connect a condenser downstream thereof.

In order to achieve rapid cooling of the reaction gas in the quench, the quench medium is generally added in liquid form. The temperature of the quench medium is preferably in the range from 0 to 250° C., especially in the range from 20 to 220° C. The spraying of the quench medium into the hot reaction gas heats and/or evaporates the quench medium. The heat needed for the heating and the evaporation of the quench medium is drawn from the reaction gas, and the reaction gas is cooled in this way. The temperature to which the reaction gas is cooled can be adjusted, for example, through the amount and the temperature of the quench medium added.

In order to set the temperature with which the quench medium is added to the quench, the quench medium is preferably passed through a heat exchanger. According to the inlet temperature of the quench medium into the heat exchanger, the quench medium can be heated or cooled therein. Cooling is required, for example, when the portion of the product stream which is used as the quench medium is withdrawn directly downstream of the quench. Heating may arise, for example, when the portion of the product stream which is used as the quench medium is withdrawn at the end of the processing zone and has a temperature lower than the desired temperature with which the quench medium is to be added to the quench. In general, however, it will be necessary to cool the quench medium before addition to the quench.

In order to compensate for solvent losses in the quench medium, it is preferred to add solvent to the quench medium before addition to the quench. Suitable solvents which are present in the quench medium are, for example, optionally halogen-substituted hydrocarbons. The solvent which is present in the quench medium is preferably selected from the group consisting of monochlorobenzene, dichlorobenzene, trichlorobenzene, hexane, benzene, 1,3,5-trimethylbenzene, nitrobenzene, anisole, chlorotoluene, o-dichlorobenzene, diethyl isophthalate, tetrahydrofuran, dimethylformamide, xylene, chloronaphthalene, decahydronaphthalene and toluene.

The proportion of isocyanate in the quench medium may be in the range from 0 to 100%. For instance, the proportion of isocyanate in the case of a pure low boiler quench is generally 0%, and 100% in the case of a pure high boiler quench. A low boiler quench is understood to mean a quench operated with essentially pure solvent as the quench medium, and a high boiler quench to mean a quench operated with essentially pure isocyanate. According to the branching-off of the quench medium in the process, however, any desired composition which comprises solvent and isocyanate is also possible.

For further treatment of the product stream, the quench is followed, in a further embodiment, by further stages for cooling the reaction gas. In the individual stages for cooling, the product stream is cooled further in each case until attainment of the desired end temperature with which the product stream is sent, for example, to a downstream workup.

The further stages for cooling which may follow downstream of the quench may, for example, be further quenches or condensers or any other stages for cooling which are known to those skilled in the art. Preferably, at least one of the stages for cooling the product stream which follows downstream of the quench is a condenser. Suitable condensers are any desired condenser designs known to those skilled in the art. Typically, the condenser used is a heat exchanger through which a cooling medium flows. The coolant used may, for example, be water or cooled solvent. In this case, the gas condenses out at least partly on the walls of the condenser. The liquid which thus arises runs down and is collected and is withdrawn from the condenser.

The condensing of the product stream is generally followed by a processing step. For example, it is possible that the condensed mixture is scrubbed in a solvent. The solvents used may, for example, be the same substances which can also be used as the quench medium.

The scrubbing transfers the isocyanate selectively into the scrubbing solution. Subsequently, preferably by rectification, the mixture obtained is separated into isocyanate, solvent, phosgene and hydrogen chloride.

Alternatively to the cooling of the product stream, it is also possible that the product stream, after leaving the quench, is fed to a separating stage. An appropriate separating stage may alternatively, however, also follow the condenser, for example. Preferably, however, the separating stage directly follows the quench. Suitable separating stages are, for example, distillation columns or scrubbers.

When the separating stage is a scrubber, the product stream leaving the quench is preferably—as described above—scrubbed with a solvent. This transfers the isocyanate selectively into the scrubbing solution. The scrubbing is then followed by a separation, preferably by means of rectification.

When the separating stage is a distillation column, the gaseous product stream is fed to the rectification column. The rectification column is preferably operated such that the temperature at the top of the rectification column is lower than the boiling temperature of the product stream. In this way, individual constituents of the product stream condense out selectively in the distillation column and can be withdrawn from the column at the bottom, via the top and optionally via side draws.

When the separating stage is a scrubber, a suitable apparatus is especially a scrubbing tower in which the isocyanate formed is removed from the gaseous product stream by condensation in an inert solvent, while excess phosgene, hydrogen chloride and if appropriate the inert medium pass through the scrubbing tower in gaseous form. The temperature of the inert solvent is preferably selected such that the carbamoyl chloride corresponding to the amine is present dissolved in the selected scrubbing medium. Particular preference is given to keeping the temperature of the inert solvent above the melting temperature of the carbamoyl chloride corresponding to the amine.

Suitable scrubbers are any desired scrubbers known to those skilled in the art. For example, it is possible to use stirred vessels or other conventional apparatus, for example columns or mixer-settler apparatus.

After it leaves the quench, the mixture of reaction gas and quench medium is generally scrubbed and worked up as described, for example, in WO-A 2007/028715.

When a condenser is used for processing of the product stream, it is preferred to withdraw the quench medium from the condenser. In the case of processing by rectification, preference is given to removing the solvent used as the quench medium. In this case, the solvent still comprises a fraction of isocyanates. The mixture of solvent and isocyanate thus removed is then used as the quench medium.

When a portion of the product stream is used as the quench medium, it is possible to branch off this portion from the product stream, for example, after the cooling. Alternatively, the portion of the product stream used as the quench medium can also be branched off from the product stream after a workup which follows the quench.

The invention is described in detail hereinafter by way of example with reference to a drawing.

BRIEF DESCRIPTION OF DRAWING

The sole FIGURE shows a schematic diagram of the process according to the invention.

A reaction gas 1 which comprises isocyanate and hydrogen chloride leaving a reactor for preparing isocyanates by reaction of the corresponding amines with phosgene in the gas phase is fed to a quench 3. Addition of a quench medium 5 to the quench 3 cools the reaction gas 1 to form a product stream 7 comprising reaction gas and quench medium. The product stream 7 generally comprises a liquid phase and a gaseous phase.

In the embodiment shown here, the product stream 7 is fed to an apparatus for phase separation 9. A suitable phase separator 9 is any desired apparatus known to those skilled in the art, in which a liquid phase can be separated from a gaseous phase.

A gas phase 11 and a liquid phase 13 are withdrawn from the apparatus for phase separation 9. The gas phase comprises generally phosgene, HCl, and possibly inert medium and solvent, and the liquid phase 13 comprises generally the isocyanate, high-boiling by-products and possibly solvent.

As a further stream, in the embodiment shown here, quench medium 15 is also withdrawn from the apparatus for phase separation 9. The quench medium 15 may possibly comprise solid particles. In general, the quench medium 15 comprises solvent and isocyanate. The quench medium 15 is fed to a heat exchanger 17 in which it is cooled to the desired feed temperature into the quench 3. Any solvent discharged with the gas phase 11 or the liquid phase 13 is replaced via a solvent feed 19. The solvent 19 may alternatively be fed upstream of the heat exchanger 17 or downstream of the heat exchanger 17. It is also possible to split the solvent stream and to feed in a portion of the solvent upstream of the heat exchanger 17 and a portion of the solvent downstream of the heat exchanger 17. According to the temperature of the solvent, the addition of the solvent 19 further cools the quench medium 15. The solvent feed 19 may be fed from any desired process stage, or solvent is added from outside.

The heat exchanger 17 is followed by at least one particle separator 21. The particle separator 21 used may, for example, be a hydrocyclone or a filter. Alternatively, it is also possible to use, as the particle separator, for example, a distillation column or an evaporator and a condenser. In the particle separator 21, any solid particles present in the quench medium 5 are removed. Depending on the particle separator 21 used, the solid particles can be withdrawn, for example, as a sludge, as a filtercake, or else as bottoms of a distillation. The solid-comprising stream is designated with reference numeral 23.

When a plurality of particle separators 21 are used, a plurality of the same type of particle separator or different particle separators can be used in series or parallel. For example, it is possible to use a plurality of filters, a plurality of hydrocyclones, or else filters and hydrocyclones. When a plurality of filters are used as the particle separator 21, it is possible, for example, to use a plurality of filters with different pore size, in which case the pore size decreases from filter to filter in flow direction of the quench medium. It may, however, also be advantageous to use a plurality of the same type of particle separator in parallel, and to regenerate them alternately. The quench medium thus freed of solid particles is then fed to the quench 3 for cooling the reaction gas 1.

In addition to the embodiment shown here, in which the quench medium 15 is withdrawn from the apparatus for phase separation 9, it is alternatively also possible to branch off a portion of the product stream 7 directly after it leaves the quench 3. It is also possible to branch off a portion of the liquid phase 13 which is withdrawn from the apparatus for phase separation 9 as the quench medium. However, it is also possible to feed the quench only via the solvent feed 19. In this case, all liquid product leaves the apparatus for phase separation as liquid phase 13.

Alternatively, it is further possible, instead of an apparatus for phase separation, to use other stages for workup. In this case, it is likewise possible to withdraw a portion of the product stream at any desired position in order to use it, after appropriate workup, for example, by condensation and particle separation, as the quench medium 5.

LIST OF REFERENCE NUMERALS

1 Reaction gas
3 Quench

5 Quench medium
7 Product stream
9 Apparatus for phase separation
11 Gas phase
13 Liquid phase
15 Quench medium
17 Heat exchanger
19 Solvent
21 Particle separator
23 Solid-comprising stream

The invention claimed is:

1. A process for preparing at least one isocyanate, the process comprising reacting at least one corresponding amine with phosgene in the gas phase, wherein the reacting comprises:
   first, mixing the amine and the phosgene and converting the amine and the phosgene to the isocyanate in a reactor;
   cooling a reaction gas which comprises isocyanate and hydrogen chloride leaving the reactor in a quench by adding a liquid quench medium to form a mixture comprising the reaction gas and the liquid quench medium as a product stream,
   wherein the quench medium comprises at least one solvent or isocyanate and is withdrawn from a workup process connected downstream of the reacting, and
   wherein solid particles are present in the quench medium and are removed before addition to the quench.

2. The process of claim 1, wherein the solid particles present in the quench medium are removed from the quench medium in a hydrocyclone, a filter, a centrifuge, or a gravitational separator.

3. The process of claim 2, wherein the filter is a screen filter, suction filter, candle filter, leaf filter, depth filter, chamber filter, or membrane filter.

4. The process of claim 1, wherein the solid particles present in the quench medium are removed from the quench medium by evaporation and recondensation.

5. The process of claim 1, wherein the quench medium comprises, as a solvent, a hydrocarbon.

6. The process of claim 1, wherein the quench medium comprises a solvent which is selected from the group consisting of monochlorobenzene, dichlorobenzene, trichlorobenzene, hexane, benzene, 1,3,5-trimethylbenzene, nitrobenzene, anisole, chlorotoluene, o-dichlorobenzene, diethyl isophthalate, tetrahydrofuran, dimethylformamide, xylene, chloronaphthalene, decahydronaphthalene, and toluene.

7. The process of claim 1, wherein the quench medium comprises at least a portion of the product stream.

8. The process of claim 1, wherein the quench is followed by at least one further stage for cooling the reaction gas.

9. The process of claim 8, wherein at least one of the stages for cooling the reaction gas which follows the quench is a condenser.

10. The process of claim 1, wherein a portion of the product stream employed as the quench medium is branched off out of the product stream after a workup which follows the quench.

11. The process of claim 10, wherein the workup which follows the quench comprises a separating stage.

12. The process of claim 11, wherein the separating stage is a distillation column or a scrubber.

13. The process of claim 1, wherein the reacting is carried out in the presence of an inert medium.

14. The process of claim 5, wherein the hydrocarbon is halogen-substituted.

15. The process of claim 2, wherein the quench medium comprises, as a solvent a hydrocarbon.

16. The process of claim 3, wherein the quench medium comprises, as a solvent a hydrocarbon.

17. The process of claim 4, wherein the quench medium comprises, as a solvent a hydrocarbon.

18. The process of claim 2, wherein the quench medium comprises a solvent which is selected from the group consisting of monochlorobenzene, dichlorobenzene, trichlorobenzene, hexane, benzene, 1,3,5-trimethylbenzene, nitrobenzene, anisole, chlorotoluene, o-dichlorobenzene, diethyl isophthalate, tetrahydrofuran, dimethylformamide, xylene, chloronaphthalene, decahydronaphthalene, and toluene.

19. The process of claim 3, wherein the quench medium comprises a solvent which is selected from the group consisting of monochlorobenzene, dichlorobenzene, trichlorobenzene, hexane, benzene, 1,3,5-trimethylbenzene, nitrobenzene, anisole, chlorotoluene, o-dichlorobenzene, diethyl isophthalate, tetrahydrofuran, dimethylformamide, xylene, chloronaphthalene, decahydronaphthalene, and toluene.

* * * * *